United States Patent
Mazzillo et al.

(10) Patent No.: US 10,416,142 B2
(45) Date of Patent: Sep. 17, 2019

(54) OPTOELECTRONIC DEVICE FOR THE SELECTIVE DETECTION OF VOLATILE ORGANIC COMPOUNDS AND RELATED MANUFACTURING PROCESS

(71) Applicant: STMicroelectronics S.R.L., Agrate Brianza (IT)

(72) Inventors: Massimo Cataldo Mazzillo, Corato (IT); Antonella Sciuto, S.G. La Punta (IT)

(73) Assignee: STMICROELECTRONICS S.R.L., Agrate Brianza (IT)

( * ) Notice: Subject to any disclaimer, the term of this patent is extended or adjusted under 35 U.S.C. 154(b) by 0 days.

(21) Appl. No.: 15/782,626

(22) Filed: Oct. 12, 2017

(65) Prior Publication Data
US 2018/0284090 A1    Oct. 4, 2018

(30) Foreign Application Priority Data

Mar. 31, 2017    (IT) .................. 102017000035910

(51) Int. Cl.
    *H01L 31/103*    (2006.01)
    *H01L 31/101*    (2006.01)
    (Continued)

(52) U.S. Cl.
    CPC ....... *G01N 33/0047* (2013.01); *G01N 21/251* (2013.01); *G01N 21/255* (2013.01);
    (Continued)

(58) Field of Classification Search
    CPC ......... H01L 31/02024; H01L 31/02327; H01L 31/1013; H01L 27/1443; H01L 27/0629;
    (Continued)

(56) References Cited

U.S. PATENT DOCUMENTS 3,831,432 A * 8/1974 Cox .................. G01N 27/414
                                                       204/419
5,576,563 A * 11/1996 Chung ............. G01N 27/4143
                                                       257/253

(Continued)

FOREIGN PATENT DOCUMENTS

DE      10 2012 213 429 A1    2/2014
WO          00/79243 A1       12/2000
WO      WO-2010112476 A1 *   10/2010 ........... G08B 17/117

OTHER PUBLICATIONS

Liu et al., "A Survey on Gas Sensing Technology," *Sensors* 12(7):9635-9665, 2012.

*Primary Examiner* — Zandra V Smith
*Assistant Examiner* — Jeremy J Joy
(74) *Attorney, Agent, or Firm* — Seed IP Law Group LLP

(57) ABSTRACT

An optoelectronic device for detecting volatile organic compounds is described, including a die with a semiconductor body, the die forming a MOSFET transistor and at least one photodiode. The optoelectronic device is optically couplable to an optical source that emits radiation with a spectrum at least partially overlapping the absorption spectrum range of the semiconductor body. The MOSFET transistor is planar and includes a gate region and a catalytic region that is arranged on the gate region such that, in the presence of a gas mixture including volatile organic compounds, the MOSFET transistor can be biased to generate an electrical signal indicating the overall concentration of the gas mixture. The photodiode generates a photocurrent that is a function of the concentration of one or more polycyclic aromatic hydrocarbons present in the gas mixture.

17 Claims, 13 Drawing Sheets

(51) Int. Cl.
*H01L 31/0232* (2014.01)
*H01L 31/02* (2006.01)
*H01L 27/144* (2006.01)
*G01N 33/00* (2006.01)
*G01N 27/414* (2006.01)
*G01N 21/84* (2006.01)
*G01N 21/33* (2006.01)
*G01N 21/31* (2006.01)
*G01N 21/25* (2006.01)

(52) U.S. Cl.
CPC .............. *G01N 21/31* (2013.01); *G01N 21/33* (2013.01); *G01N 21/8422* (2013.01); *G01N 27/4141* (2013.01); *G01N 33/0031* (2013.01); *G01N 33/0067* (2013.01); *H01L 27/1443* (2013.01); *H01L 31/02024* (2013.01); *H01L 31/02327* (2013.01); *H01L 31/103* (2013.01); *H01L 31/1013* (2013.01)

(58) Field of Classification Search
CPC ...... H01L 31/103; H01L 31/10; G01N 33/047; G01N 33/0067; G01N 33/0031; G01N 21/61; G01N 21/3504; G01N 27/414; G01N 27/4141; G01N 2021/3513; G01N 33/0047
See application file for complete search history.

(56) References Cited

U.S. PATENT DOCUMENTS

| | | | | |
|---|---|---|---|---|
| 5,671,914 | A * | 9/1997 | Kalkhoran | H01L 27/14645 257/437 |
| 5,726,440 | A * | 3/1998 | Kalkhoran | H01L 31/103 250/214.1 |
| 6,028,331 | A * | 2/2000 | Mastromatteo | G01N 27/12 257/253 |
| 6,051,854 | A * | 4/2000 | Vigna | G01N 27/12 204/424 |
| 6,330,464 | B1 * | 12/2001 | Colvin, Jr. | A61B 5/0031 128/903 |
| 2005/0097941 | A1 * | 5/2005 | Sandvik | G01N 27/4141 73/31.06 |
| 2006/0123885 | A1 * | 6/2006 | Yates | G01N 27/414 73/31.03 |
| 2006/0208917 | A1 * | 9/2006 | Schumann | G01N 21/3151 340/632 |
| 2007/0200067 | A1 * | 8/2007 | Yoshida | G01N 21/33 250/373 |
| 2008/0157152 | A1 * | 7/2008 | Shim | H01L 27/14603 257/292 |
| 2008/0220535 | A1 * | 9/2008 | LeBoeuf | B82Y 30/00 436/164 |
| 2009/0009769 | A1 * | 1/2009 | Uber | G01N 21/1702 356/437 |
| 2009/0140367 | A1 * | 6/2009 | Iwai | H01L 27/1443 257/462 |
| 2009/0230498 | A1 * | 9/2009 | Iwai | H01L 27/1443 257/461 |
| 2010/0127314 | A1 * | 5/2010 | Frach | H01L 27/1443 257/292 |
| 2012/0199826 | A1 * | 8/2012 | Nakahara | G01J 1/1626 257/43 |
| 2014/0175523 | A1 * | 6/2014 | Feyh | G01N 27/4146 257/253 |
| 2014/0233039 | A1 * | 8/2014 | Takahashi | G01N 21/253 356/519 |
| 2014/0284669 | A1 * | 9/2014 | Arcuri | H01L 27/14623 257/290 |
| 2014/0290338 | A1 * | 10/2014 | Kim | G01N 33/0009 73/31.06 |
| 2015/0101395 | A1 * | 4/2015 | Dehe | G01N 29/2418 73/24.02 |
| 2015/0308962 | A1 * | 10/2015 | Mazzillo | G01N 21/85 250/208.2 |
| 2016/0231244 | A1 * | 8/2016 | Camargo | G01N 21/0303 |
| 2016/0349108 | A1 * | 12/2016 | Mazzillo | H01L 31/1013 |
| 2017/0138879 | A1 * | 5/2017 | Akiyama | G01N 27/129 |
| 2017/0219479 | A1 * | 8/2017 | Bilenko | G01N 21/031 |
| 2017/0236851 | A1 * | 8/2017 | Mazzillo | G01N 21/85 257/77 |
| 2017/0296771 | A1 * | 10/2017 | Scharmer | A61M 16/0891 |
| 2017/0314989 | A1 * | 11/2017 | Mazzillo | G01J 1/429 |

* cited by examiner

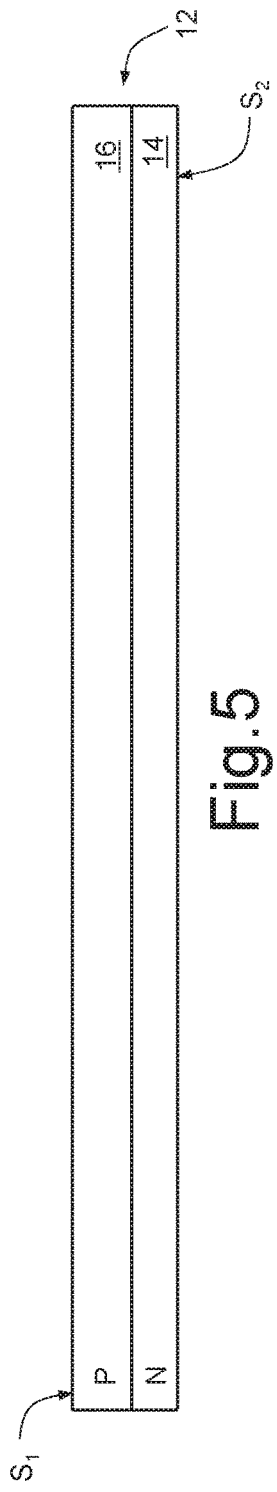
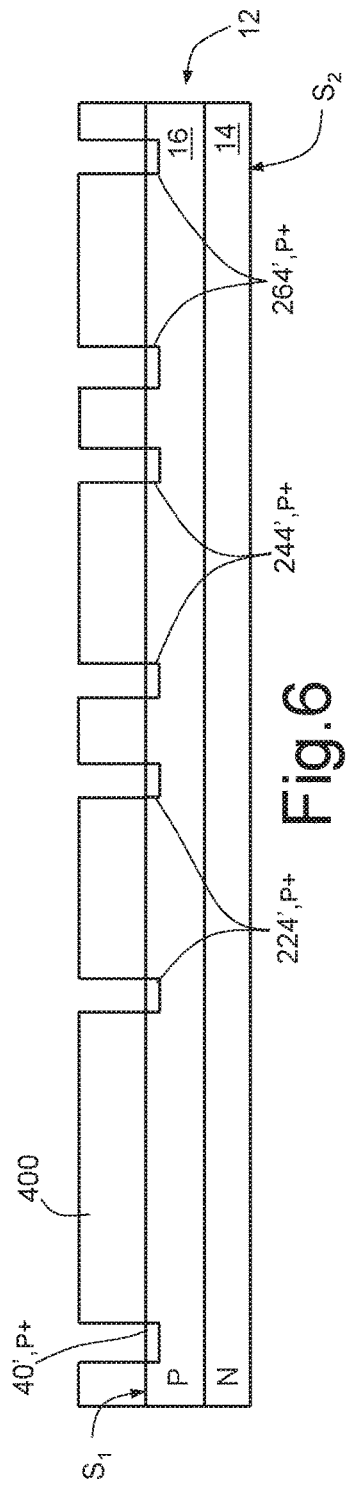
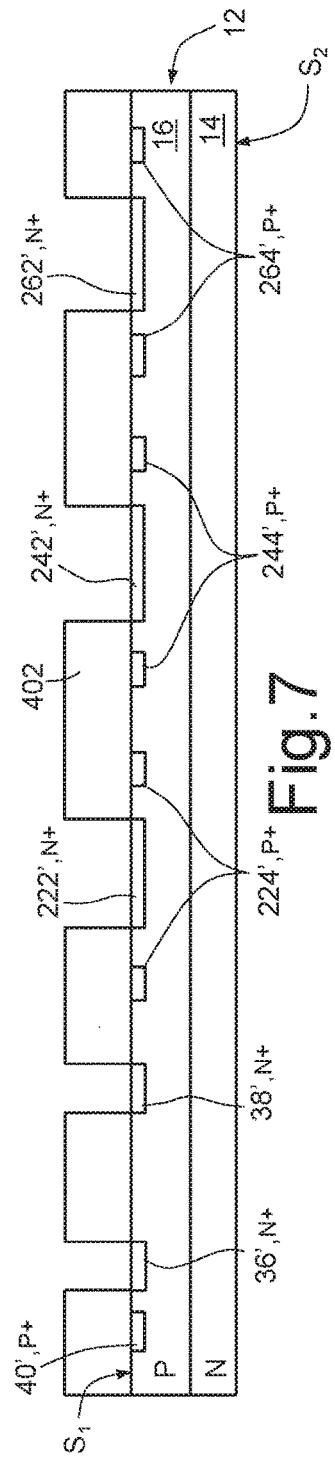

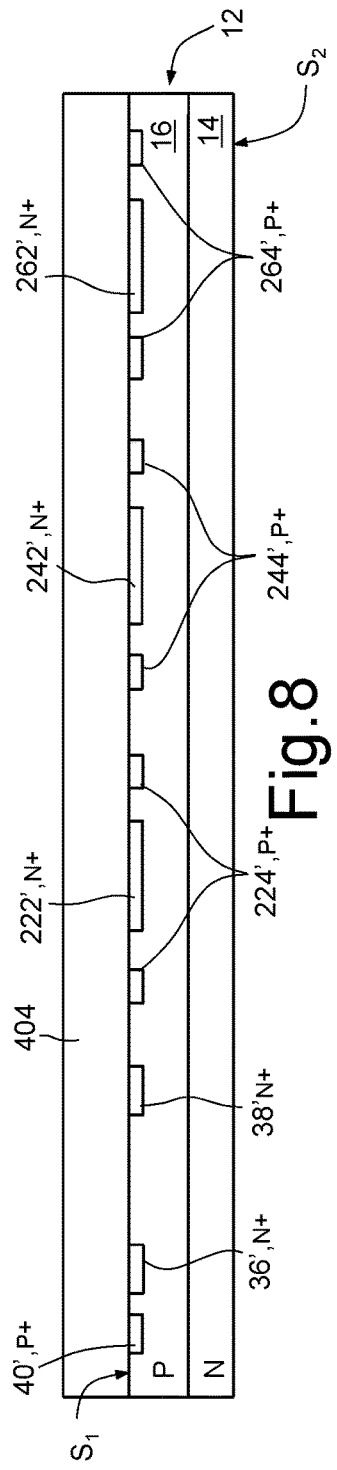
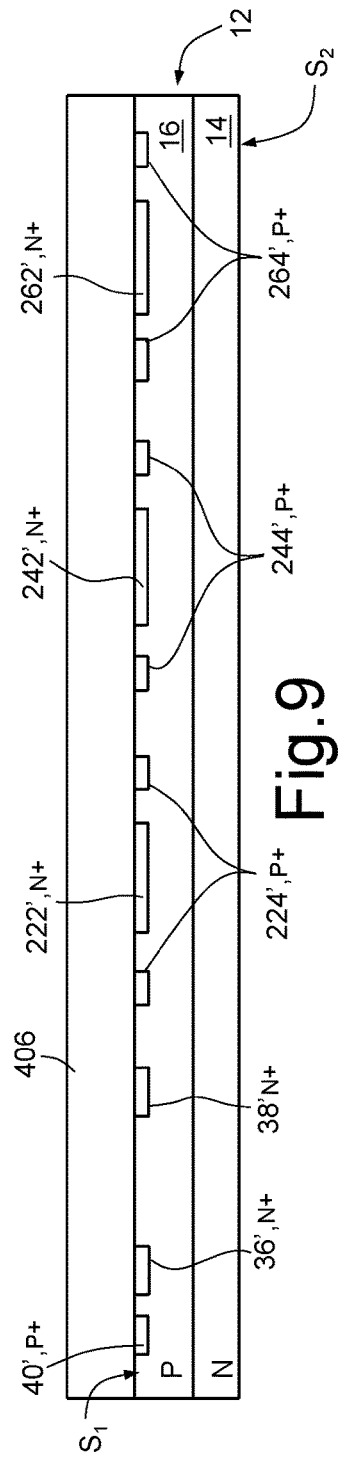
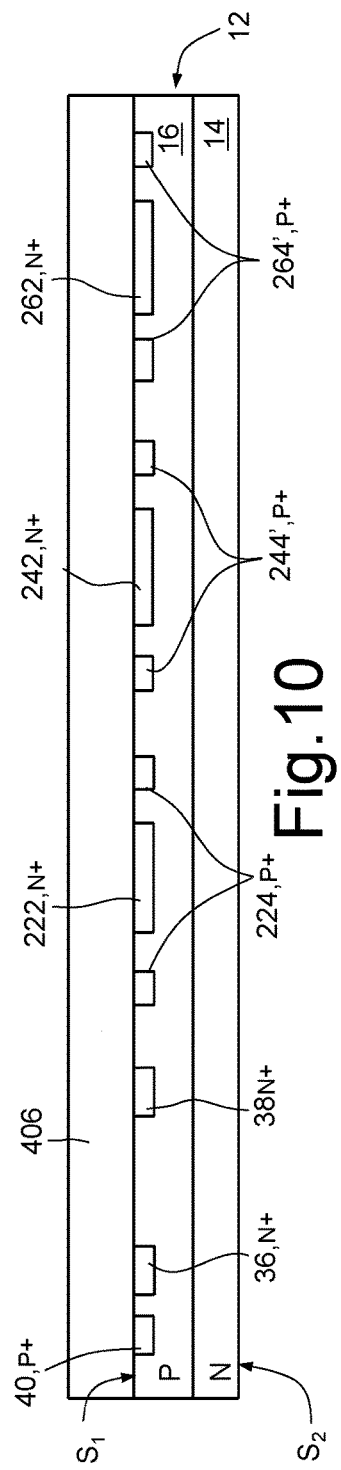

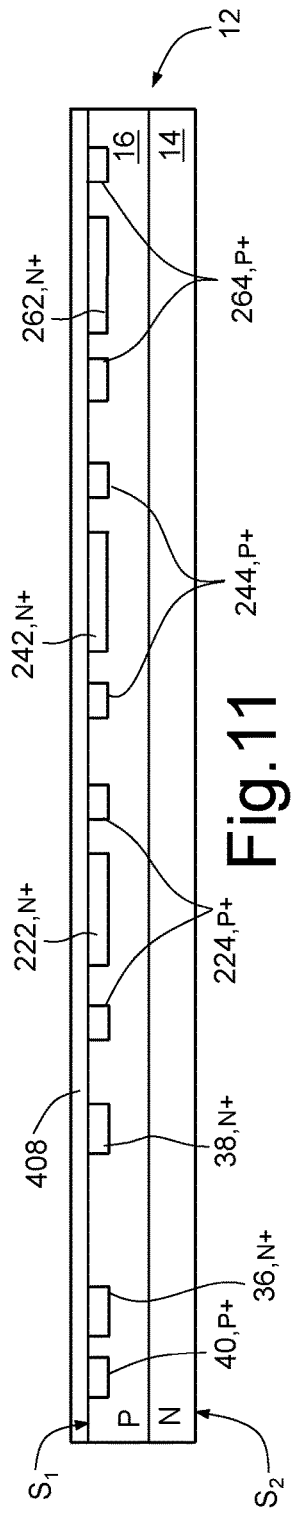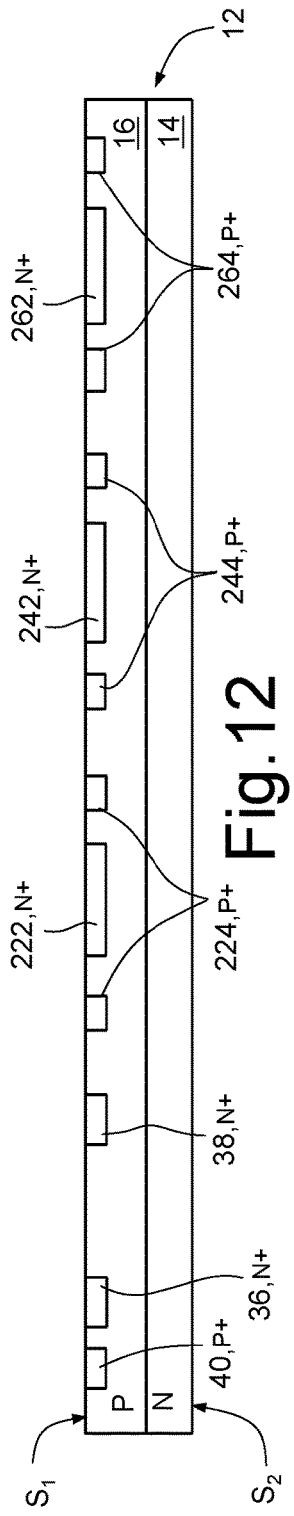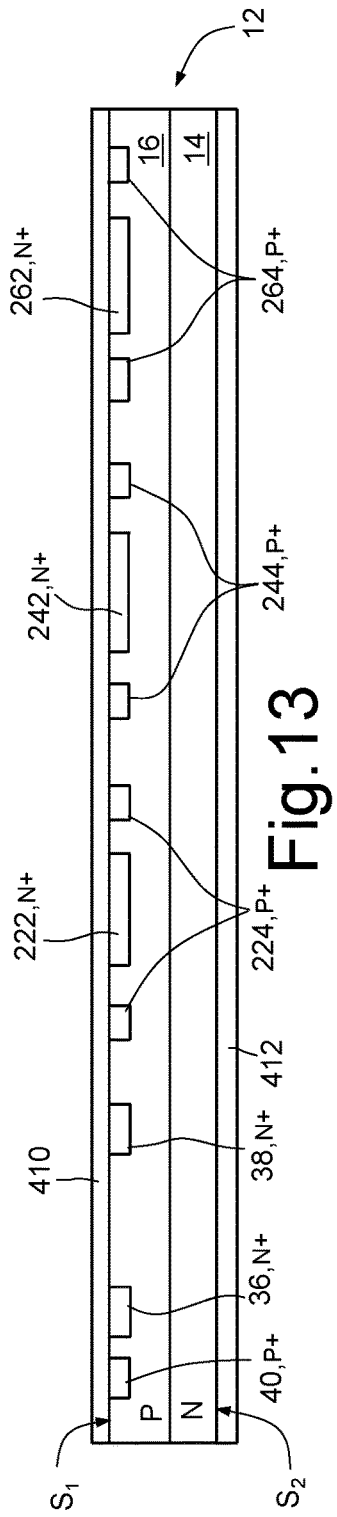

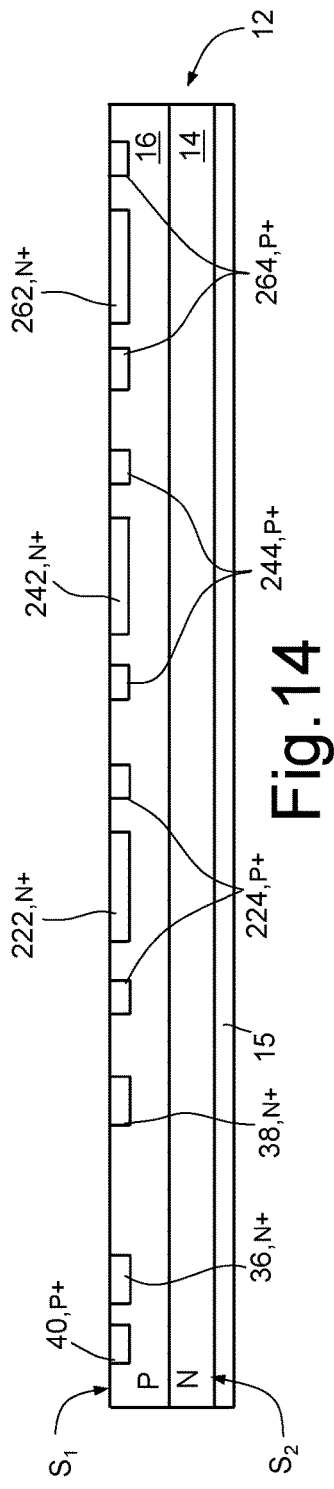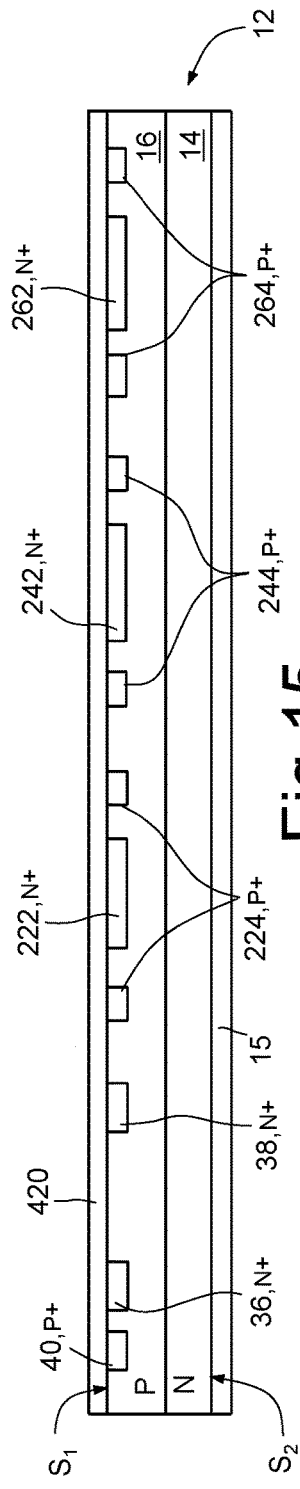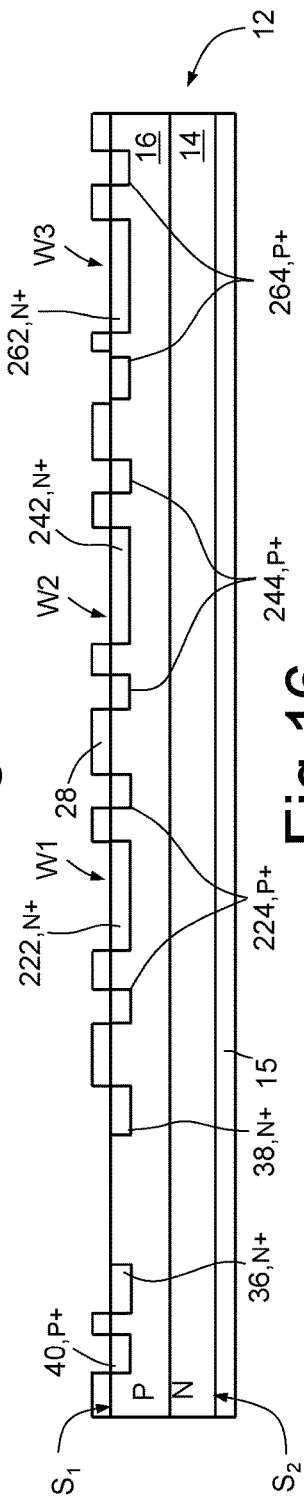

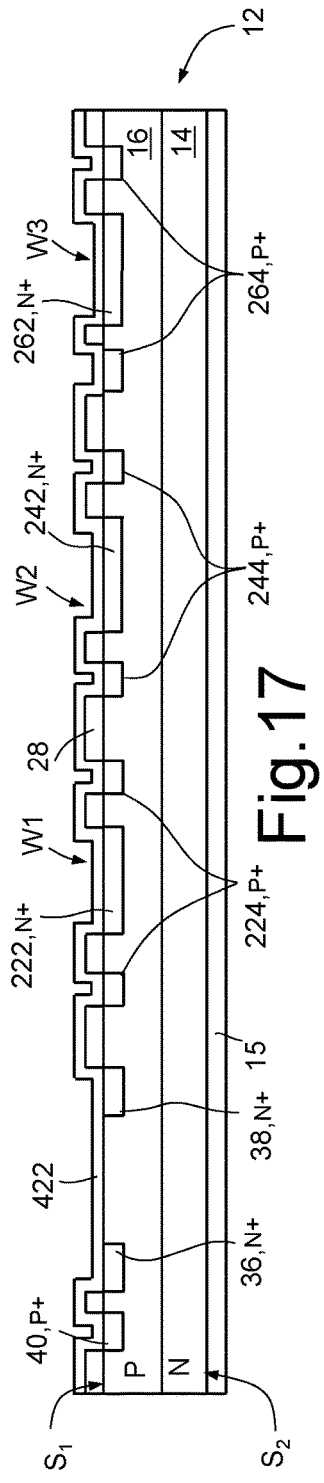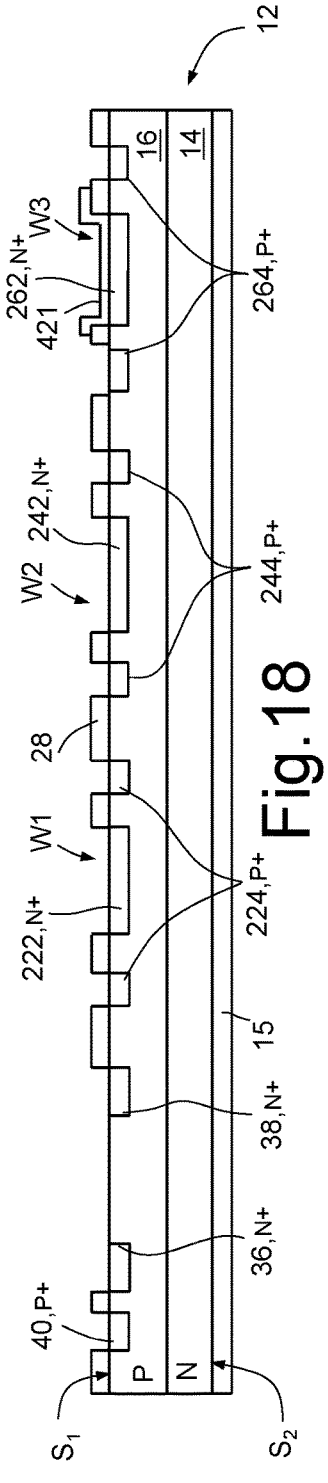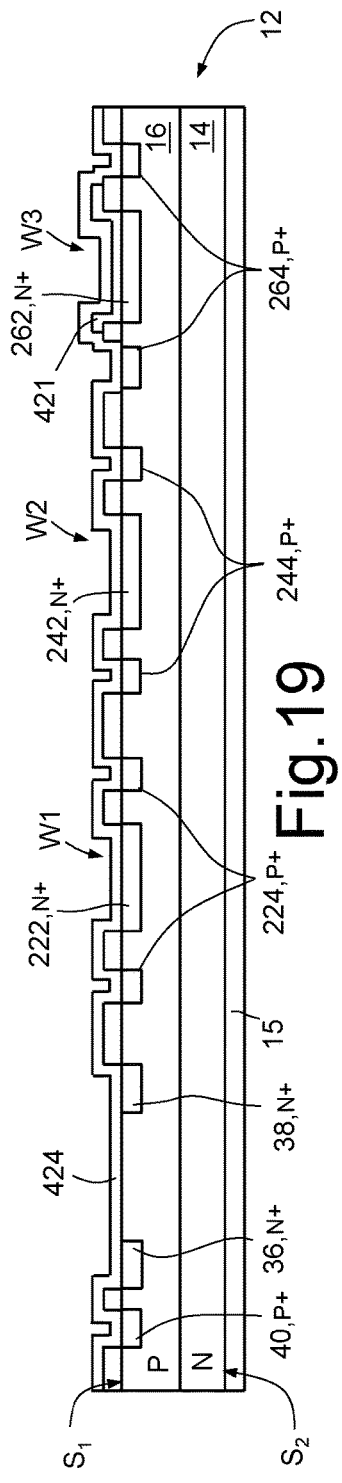

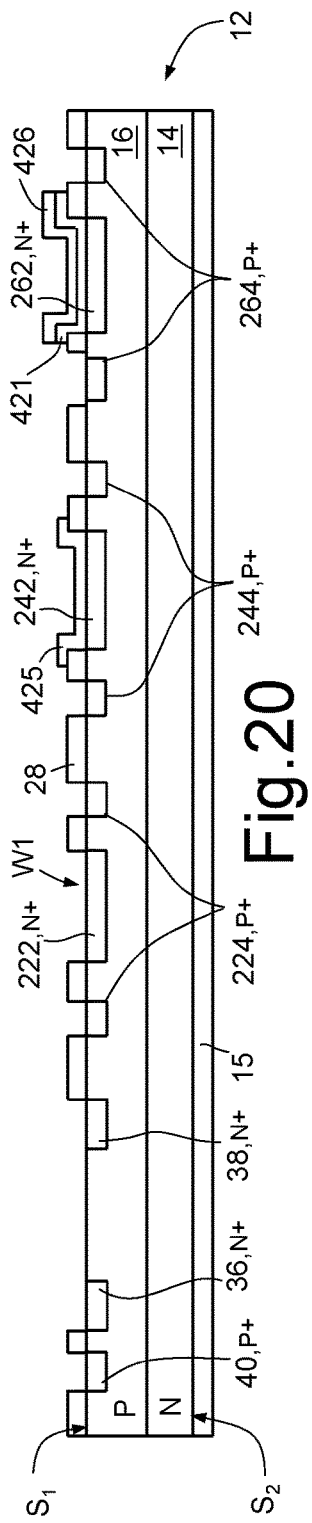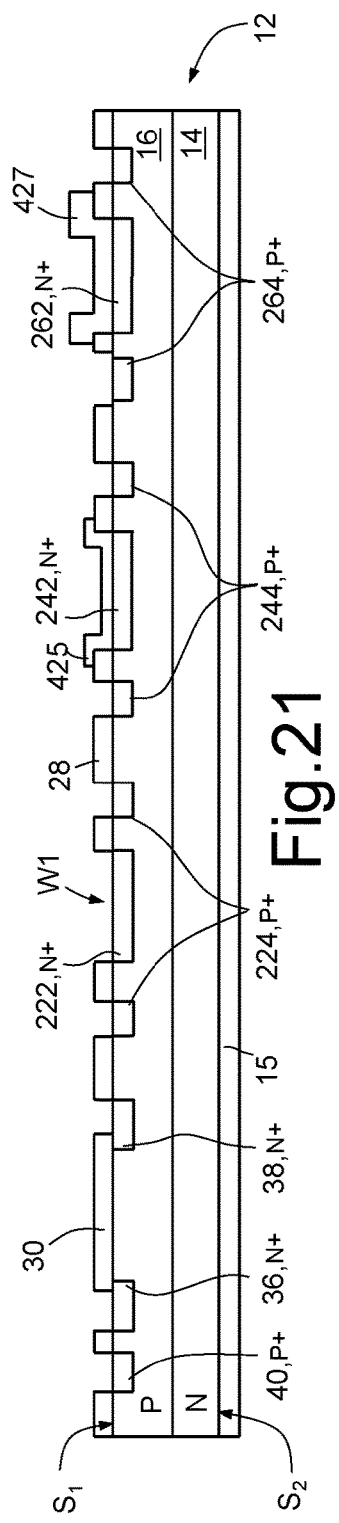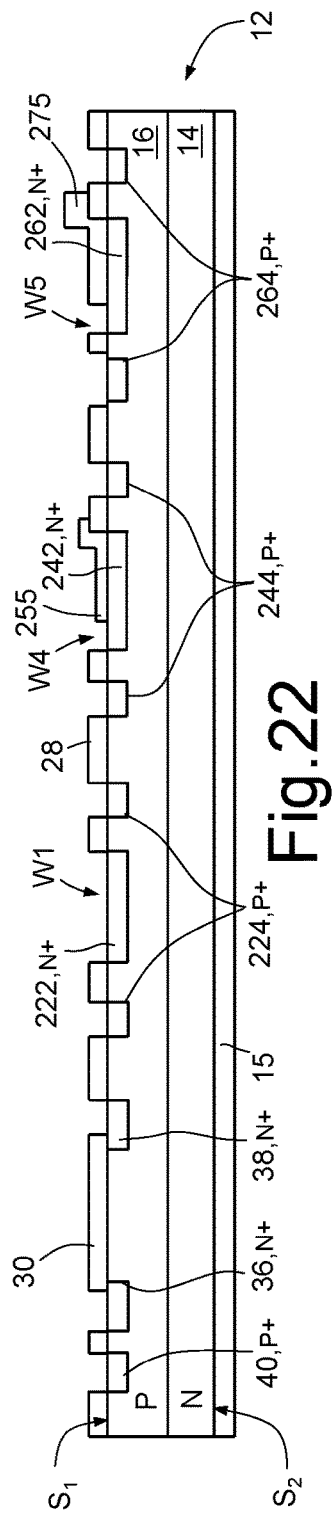

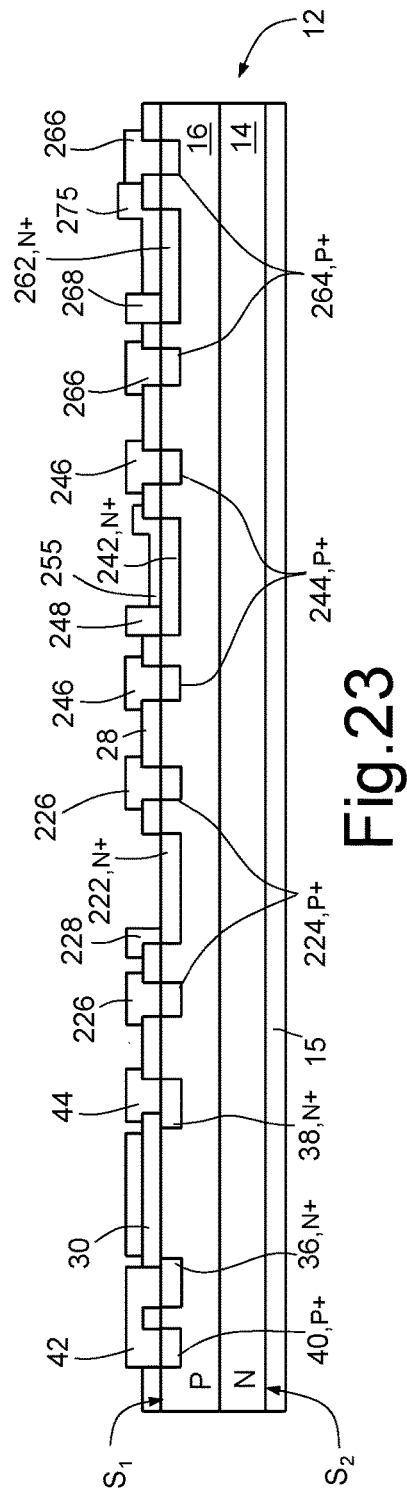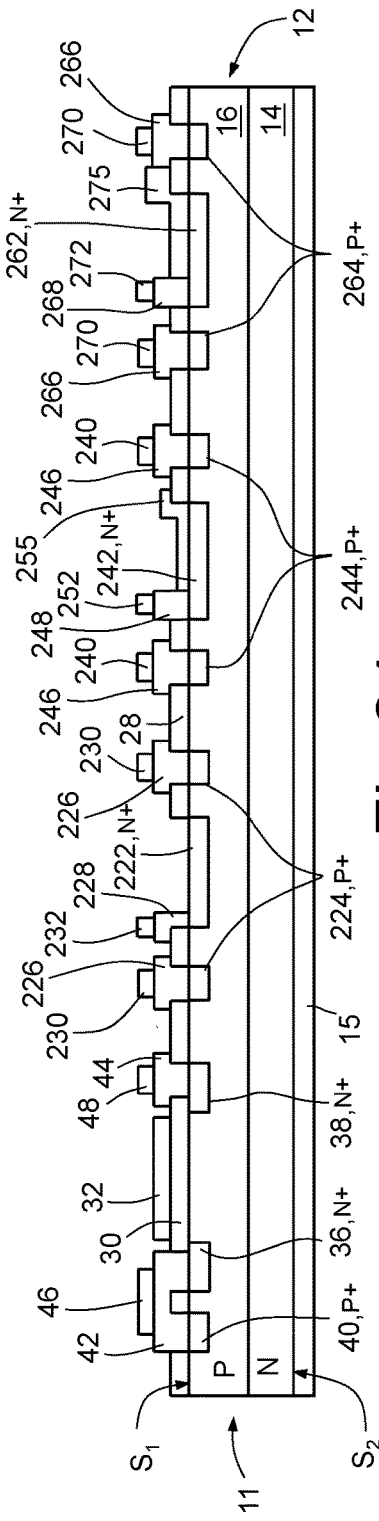

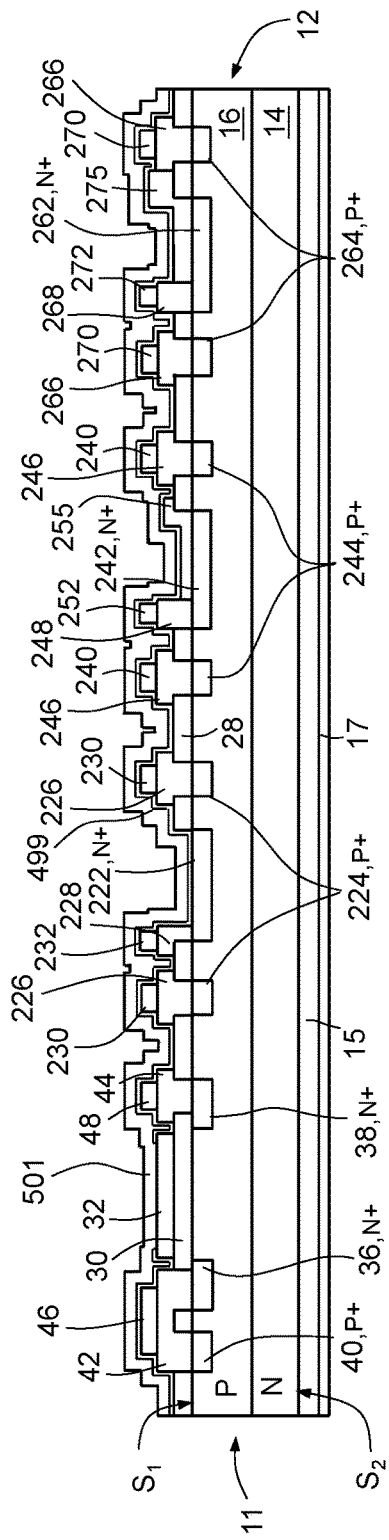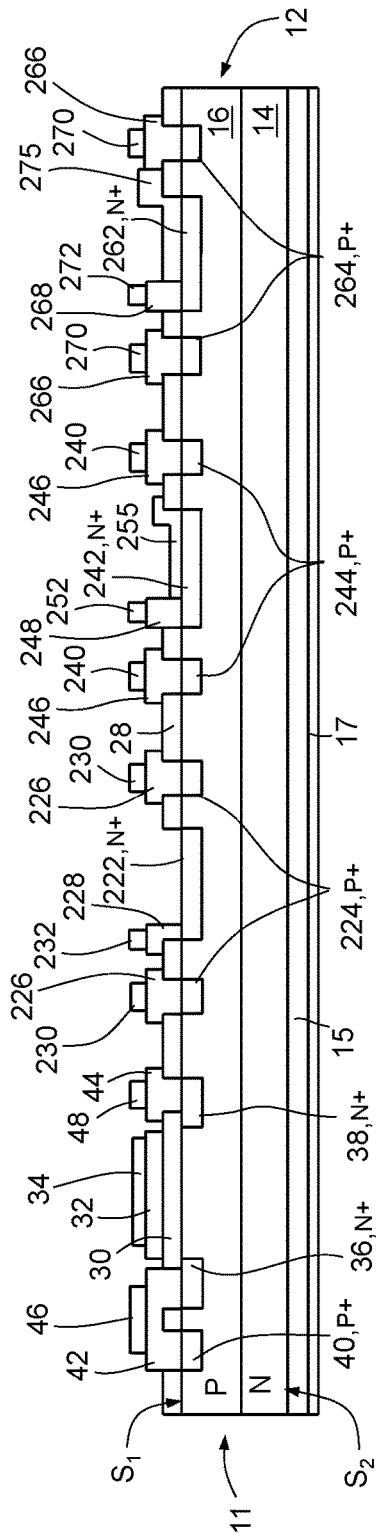

OPTOELECTRONIC DEVICE FOR THE SELECTIVE DETECTION OF VOLATILE ORGANIC COMPOUNDS AND RELATED MANUFACTURING PROCESS

BACKGROUND

Technical Field

The present disclosure relates to an optoelectronic device for the selective detection of volatile organic compounds (VOC) and the related manufacturing process.

Description of the Related Art

As is well known, there is nowadays a need for sensors that are able to detect volatile organic compounds, including (inter alia) polycyclic aromatic hydrocarbons (PAH), which are known to be harmful to human health.

In consideration of this, it is currently possible to obtain solid-state systems for detecting volatile organic compounds that are characterized by being compact and low-cost, but they are not very selective of the different components in the volatile organic compounds being analyzed. There are known techniques based on multiple detection at different temperatures (between 100° C. and 400° C.) intended to at least partially increase selectivity. Conversely, highly selective systems for detecting volatile organic compounds are also available, based on high-precision liquid chromatography. However, such detection systems are very large and expensive, and as such are limited to use in analysis laboratories.

BRIEF SUMMARY

One or more embodiments of the present disclosure provide an optoelectronic device for detecting volatile organic compounds that at least partially addresses the drawbacks in the prior art.

Some embodiments of the present disclosure provide for an optoelectronic device and a manufacturing process. One embodiment of the present disclosure is an optoelectronic device for detecting volatile organic compounds, including:

a die including a semiconductor body made of a semiconductor material with an absorption spectrum range, the optoelectronic device being optically couplable to an optical source designed to emit radiation with a spectrum at least partially overlapping the absorption spectrum range;

a MOSFET transistor formed in the semiconductor body, wherein the MOSFET transistor is planar and includes a gate region and a catalytic region that is arranged on the gate region such that, in the presence of a gas mixture including volatile organic compounds, the MOSFET transistor is configured be biased to generate an electrical signal indicating an overall concentration of the gas mixture within a volume; and a first photodiode configured to generate, when the optoelectronic device is optically coupled to set optical source, a first photocurrent that is a function of a concentration of one or more polycyclic aromatic hydrocarbons present in the gas mixture.

BRIEF DESCRIPTION OF THE SEVERAL VIEWS OF THE DRAWINGS

The disclosure is further described below with reference to embodiments of same, which are provided purely as non-limiting examples, and to the attached drawings, in which:

FIGS. 5-28 are schematic cross sections of an embodiment of the present optoelectronic device during successive phases of a manufacturing process.

DETAILED DESCRIPTION

Figure 1:
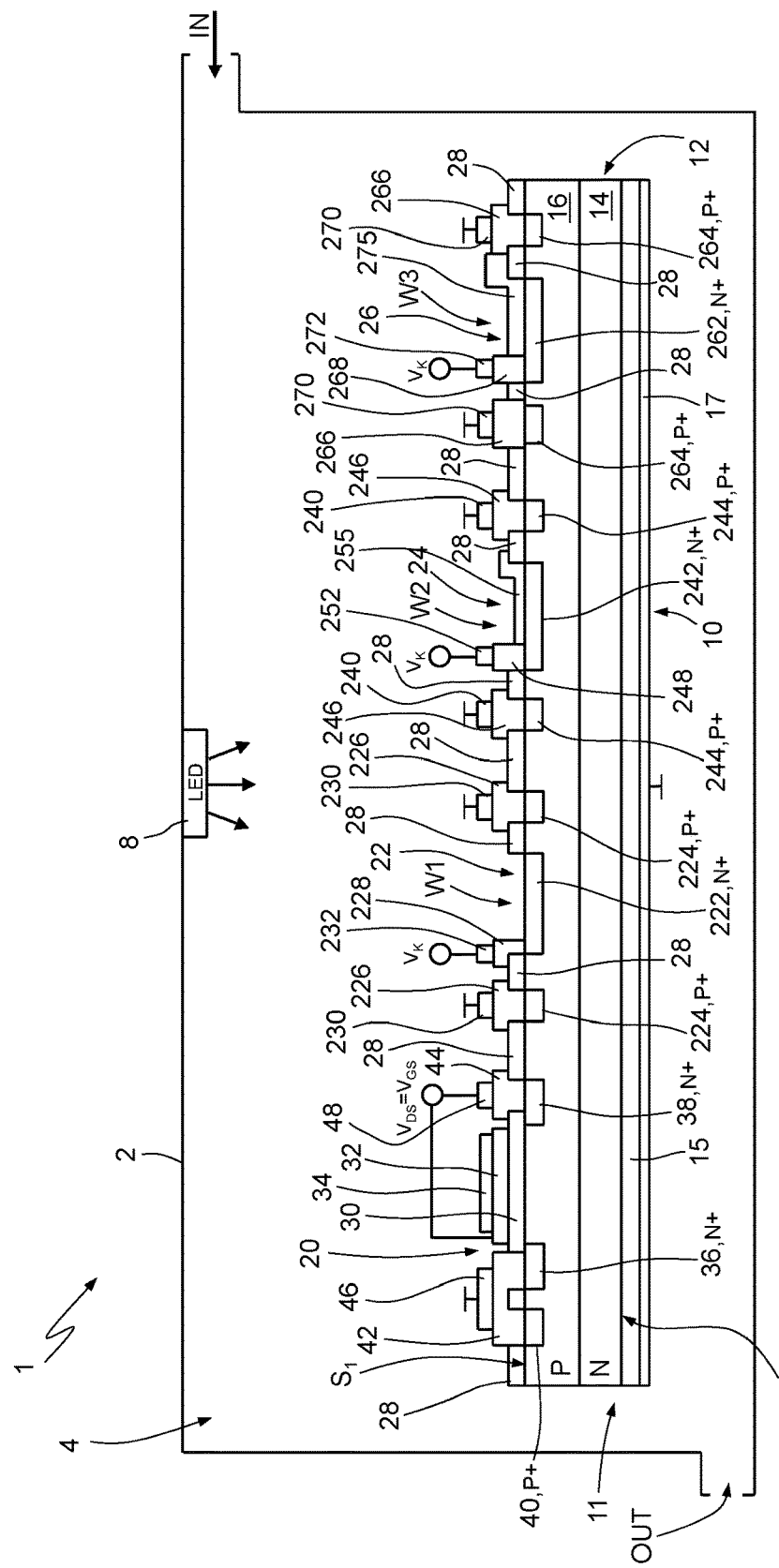
FIG. 1 (not the scale) is a schematic cross section of an embodiment of a detection system including the present optoelectronic device.

FIG. 1 (not to scale) shows a detection system 1 including a container 2 that delimits a chamber 4 and has an input aperture IN and an output aperture OUT. In particular, a gas mixture can move in and out of the chamber 4, respectively through the input aperture IN and the output aperture OUT.

The detection system 1 also includes a light source 8 and an optoelectronic device 10, which are both arranged in the chamber 4. In particular, the light source 8 is attached to the container 2 and arranged above and away from the optoelectronic device 10.

The light source 8 emits ultraviolet radiation, i.e., radiation with a wavelength of less than 400 nm. In particular, the light source 8 emits radiation with a wavelength within the 200-400 nm range, for example.

The optoelectronic device 10 is formed in a die 11 and includes a semiconductor body 12 that is formed for example from 4H silicon-carbide polytype (4H—SiC) and is delimited above and below by first and second surfaces S1, S2 respectively.

The semiconductor body 12 includes an N-type substrate 14 that is delimited below by the second surface S2 and is for example 350 µm thick. Furthermore, the substrate 14 is for example doped with nitrogen and has for example a doping level of $1*10^{19}$ cm-3.

Furthermore, the semiconductor body 12 includes an epitaxial layer 16 that is arranged on the substrate 14, forms the first surface S1 and is P-type. The epitaxial layer 16 is for example 1 µm thick and has for example a doping level of $5*10^{16}$ cm-3. Furthermore, the epitaxial layer 16 is for example doped with aluminum.

There is a lower conductive region 15, made for example from nickel silicide, beneath the second surface S2. Furthermore, beneath the lower conductive region 15 and in direct contact with same, there is a lower metallization 17 that, although not shown, may be formed by a multilayer structure including three layers arranged in succession and made respectively of titanium, nickel and gold.

The optoelectronic device 10 includes a MOSFET transistor 20 and first, second and third photodiodes 22, 24, 26, which are built into the die 11 and are staggered laterally in relation to one another such that the first photodiode 22 is interposed between the MOSFET transistor 20 and the second photodiode 24, while the second photodiode 24 is interposed between the first photodiode 22 and the third photodiode 26.

The optoelectronic device 10 also includes a dielectric region 28, hereinafter referred to as the field oxide region 28. The field oxide region 28 is for example made of TEOS oxide and is arranged above the first surface S1, in contact with the epitaxial layer 16.

More specifically, the MOSFET transistor 20 is planar and includes an insulating region 30 that is formed for example by one or more dielectric layers and extends through the field oxide region 28 above the first surface S1, such as to touch the epitaxial layer 16. Seen from above, the shape of the insulating region 30 may for example be polygonal (for example rectangular).

The MOSFET transistor 20 also includes a gate region 32 that is made of a conductive material and is arranged above and in direct contact with the insulating region 30. The MOSFET transistor 20 also includes a region 34, hereinafter referred to as the catalytic region 34. The catalytic region 34 is formed by a catalytic material (for example, a metal such as palladium, tungsten or iridium). Furthermore, the catalytic region 34 is arranged in direct contact with the gate region 32.

The MOSFET transistor 20 also includes a source region 36 and a drain region 38, which are N+ type and have a doping level of 1*1019 cm-3, for example.

More specifically, the source region 36 and the drain region 38 are arranged inside the epitaxial layer 16, from the first surface S1, and are laterally staggered in relation to the insulating region 30. Indeed, the source region 36 and the drain region 38 are arranged on opposite sides of the insulating region 30, approximately symmetrically. A first peripheral portion of the insulating region 30 is arranged above and in direct contact with a portion of the source region 36, while a second peripheral region of the insulating region 30 is arranged above and in direct contact with a portion of the drain region 38. A central portion of the insulating region 30 is positioned beneath the gate region 32, as mentioned previously.

The MOSFET transistor 20 also includes a P+ enriched region 40 that is arranged inside the epitaxial layer 16 from the first surface S1, and is laterally staggered in relation to the source region 36. In particular, the enriched region 40 and the drain region 38 are arranged on opposite sides in relation to the source region 36. The thickness of the enriched region 40 is for example between 0.1 µm and 0.4 µm and has a peak doping level of $1*10^{19}$ cm$^{-3}$, for example. The enriched region 40 is hereinafter referred to as the enriched transistor region 40. This region performs a contact function.

The MOSFET transistor 20 also includes a source contact region 42 and a drain contact region 44, which are for example made of nickel silicide. In particular, the source contact region 42 extends through the field oxide region 28 such that same is in contact with the enriched region 40 and the source region 36, while the drain contact region 44 extends through the field oxide region 28 such that same is in contact with the drain region 38.

A source metallization 46 and a drain metallization 48 are arranged above and in direct contact with a source contact region 42 and the drain contact region 44 respectively. In use, the source metallization 46 may be connected to ground, as may the lower metallization 17. Furthermore and as shown schematically in FIG. 1, the drain metallization 48 may be connected electrically to the gate region 32. The drain metallization 48 and the gate region 32 can thus be brought to a voltage VDS=VGS, in which VGS represents the gate-source voltage of the MOSFET transistor 20, which therefore works above-threshold, like a diode.

The first photodiode 22 includes a first N+ cathode region 222. In particular, the first cathode region 222 is arranged in the epitaxial layer 16 from the first surface S1, is for example between 0.1 µm and 0.4 µm thick and has a peak doping level of $1*10^{19}$ cm$^{-3}$, for example. Furthermore, when seen from above, the first cathode region 222 is circular or polygonal in shape (for example quadrangular). Additionally, the field oxide region 28 forms a first window W1 above the first cathode region 222, such as to expose the first cathode region 222.

The first photodiode 22 also includes a respective P+ enriched region 224, hereinafter referred to as the first enriched anode region 224. More specifically, the first enriched anode region 224 is arranged in the epitaxial layer 16 from the first surface S1, is for example between 0.1 µm and 0.4 µm thick and has a peak doping level of $1*10^{19}$ cm$^{-3}$, for example. Without limitation, the first enriched anode region 224 laterally surrounds and is separated from the entire first cathode region 222.

The first photodiode 22 also includes a first anode contact region 226 and a first cathode contact region 228, which are for example made of nickel silicide. In particular, the first anode contact region 226 extends through the field oxide region 28 to come into contact with the first enriched anode region 224. The first cathode contact region 228 is arranged at least partially inside the first window W1, to come into contact with the first cathode region 222.

The first photodiode 22 also includes a first anode metallization 230 arranged above and in direct contact with the first anode contact region 226, and a first cathode metallization 232 arranged above and in direct contact with the first cathode contact region 228.

The second photodiode 24 includes a second N+ cathode region 242. In particular, the second cathode region 242 is arranged in the epitaxial layer 16 from the first surface S1, is for example between 0.1 µm and 0.4 µm thick and has a peak doping level of $1*10^{19}$ cm$^{-3}$, for example. Furthermore, when seen from above, the second cathode region 242 is circular or polygonal in shape (for example quadrangular). Additionally, the field oxide region 28 forms a second window W2 above the second cathode region 242.

The second photodiode 24 also includes a respective P+ enriched region 244, hereinafter referred to as the second enriched anode region 244. More specifically, the second enriched anode region 244 is arranged in the epitaxial layer 16 from the first surface S1, is for example between 0.1 µm and 0.4 µm thick and has a peak doping level of $1*10^{19}$ cm$^{-3}$, for example. Without limitation, the second enriched anode region 244 laterally surrounds and is separated from the entire second cathode region 242.

The second photodiode 24 also includes a second anode contact region 246 and a second cathode contact region 248, which are for example made of nickel silicide. In particular, the second anode contact region 246 extends through the field oxide region 28 to come into contact with the second enriched anode region 244. The second cathode contact region 248 is arranged inside the second window W2 to come into lateral contact with a corresponding portion of the field oxide region 28, and is arranged above and in direct contact with a portion of the second cathode region 242 oriented (without limitation) towards the first photodiode 22.

The second photodiode 24 also includes a second anode metallization 240 arranged above and in direct contact with the second anode contact region 246, and a second cathode metallization 252 arranged above and in direct contact with the second cathode contact region 248.

The second photodiode 24 also includes another region 255, hereinafter referred to as the first filtering region 255. More specifically, the first filtering region 255 is for example made of silicon nitride ($Si_3N_4$) and is arranged inside the second window W2 to come into lateral contact with the second cathode contact region 248 and a corresponding portion of the field oxide region 28, and is arranged above and in direct contact with a portion of the second cathode region 242 oriented towards the third photodiode 26. More specifically, the portion of the second cathode region 242 that is not beneath the cathode contact region 248 is entirely beneath the first filtering region 255.

The first filtering region 255 is for example 280 nm thick and acts as a first optical filter, as described in greater detail below.

The third photodiode 26 includes a third N+ cathode region 262. In particular, the third cathode region 262 is arranged in the epitaxial layer 16 from the first surface S1, is for example between 0.1 μm and 0.4 μm thick and has a peak doping level of $1*10^{19}$ cm$^{-3}$, for example. Furthermore, when seen from above, the third cathode region 262 is circular or polygonal in shape (for example quadrangular). Additionally, the field oxide region 28 forms a third window W3 above the third cathode region 262.

The third photodiode 26 also includes a respective P+ enriched region 264, hereinafter referred to as the third enriched anode region 264. More specifically, the third enriched anode region 264 is arranged in the epitaxial layer 16 from the first surface S1, is for example between 0.1 μm and 0.4 μm thick and has a peak doping level of $1*10^{19}$ cm$^{-3}$, for example. Without limitation, the third enriched anode region 264 laterally surrounds and is separated from the entire third cathode region 262.

The third photodiode 26 also includes a third anode contact region 266 and a third cathode contact region 268, which are for example made of nickel silicide. In particular, the third anode contact region 266 extends through the field oxide region 28 to come into contact with the third enriched anode region 264. The third cathode contact region 268 is arranged inside the third window W3 to come into lateral contact with a corresponding portion of the field oxide region 28, and is arranged above and in direct contact with a portion of the third cathode region 262 oriented (without limitation) towards the second photodiode 24.

The third photodiode 26 also includes a third anode metallization 270 arranged above and in direct contact with the third anode contact region 266, and a third cathode metallization 272 arranged above and in direct contact with the third cathode contact region 268.

The third photodiode 26 also includes another region 275, hereinafter referred to as the second filtering region 275.

More specifically, the second filtering region 275 is made for example from silicon nitride and is arranged inside the third window W3 to come into lateral contact with the third cathode contact region 268 and a corresponding portion of the field oxide region 28, and is arranged entirely above and in direct contact with the portion of the third cathode region 262 not beneath the third cathode contact region 268.

More specifically, the second filtering region 275 is for example 480 nm thick and acts as a second optical filter, as described in greater detail below. Without limitation, both the first and the second optical filters work on the basis of the physical principle of absorption, rather than interference.

In practice, the epitaxial layer 16 forms the anode regions of first, second and third p-n junctions with the first, second and third cathode regions 222, 242, 262 respectively.

In use, the first, second and third anode metallizations 230, 240, 270 may be connected to ground, while the first, second and third cathode metallizations 232, 252, 272 may be brought to a positive voltage VK. Consequently, the aforementioned first, second and third p-n junctions are inversely biased. Furthermore, by virtue of the doping previously described, the empty regions of the first, second and third p-n junctions are arranged primarily in the epitaxial layer 16.

Operation of the optoelectronic device 10 is described below with reference to a case in which the whole of the chamber 4 contains, purely by way of example, a gas mixture that includes molecules of methane and the following molecules of polycyclic aromatic hydrocarbons: benzene molecules, naphthalene molecules and anthracene molecules. In this regard, methane, and in general other volatile organic compounds other than polycyclic aromatic hydrocarbons, has an absorption spectrum with non-zero components mainly in the infrared range only, i.e., for wavelengths greater than 700 nm. Conversely, polycyclic aromatic hydrocarbons have absorption spectra to a first approximation in the 200-400 nm range, i.e., zero outside that range, to a first approximation. In particular, benzene has an absorption peak at 255 nm, while naphthene has an absorption peak at 286 nm and anthracene has an absorption peak at 375 nm. Furthermore, to a first approximation, the absorption spectra of benzene, naphthalene and anthracene have cut-off wavelengths (corresponding to residual absorption of less than 1%) of approximately λcutoff_1=280 nm, λcutoff_2=310 nm and λcutoff_2=380 nm respectively.

Figure 2:
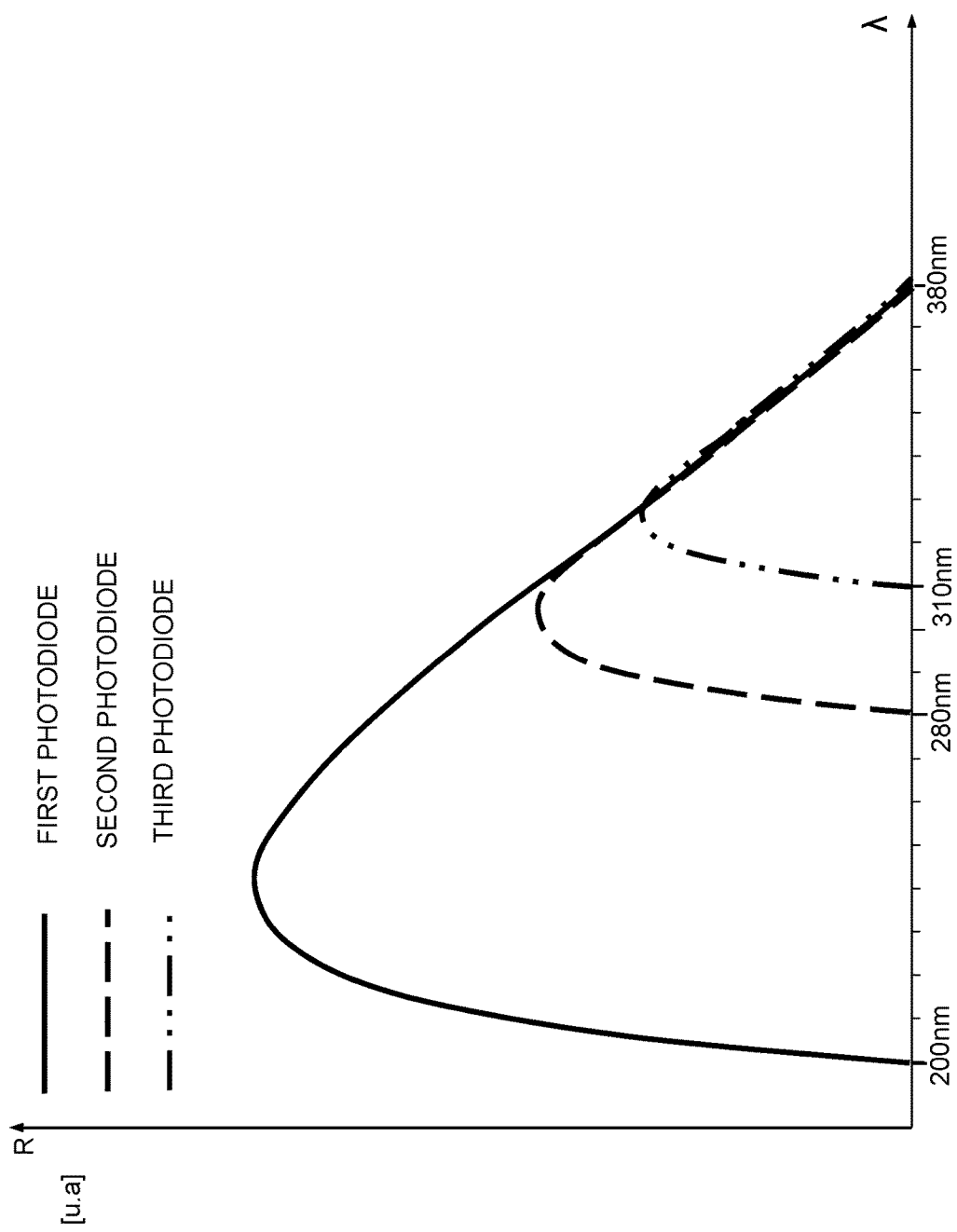
FIG. 2 shows example trends of the spectral responses of three different photodiodes, as a function of wavelength.

Operation of the optoelectronic device 10 is also described observing that, to a first approximation, the thicknesses of the first and second filtering regions 255, 275 are such that the spectral responsivities of the second and third photodiodes 24, 26 are of the type shown in FIG. 2, which also shows the spectral response of the first photodiode 22, which has no optical filter. The spectral response of the first photodiode 22 therefore depends directly on the absorption spectrum of the material used to make the semiconductor body 12. In this regard, silicon carbide is able to absorb radiation at wavelengths less than approximately 380 nm, and is thus substantially transparent for radiation at wavelengths greater than 380 nm.

From a quantitative point of view, the first optical filter acts as a highpass filter and filters, to a first approximation, radiation at wavelengths less than λτ1=280 nm (approximately equal to the cut-off wavelength λcutoff_1 of the absorption spectrum of benzene), i.e., for λτ1<280 nm the transmittance is for example less than 1%. The second optical filter also acts as a highpass filter and filters, to a first approximation, radiation at wavelengths less than λτ2=310 nm (approximately equal to the cut-off wavelength λcutoff_2 of the absorption spectrum of naphthalene).

Figure 3:
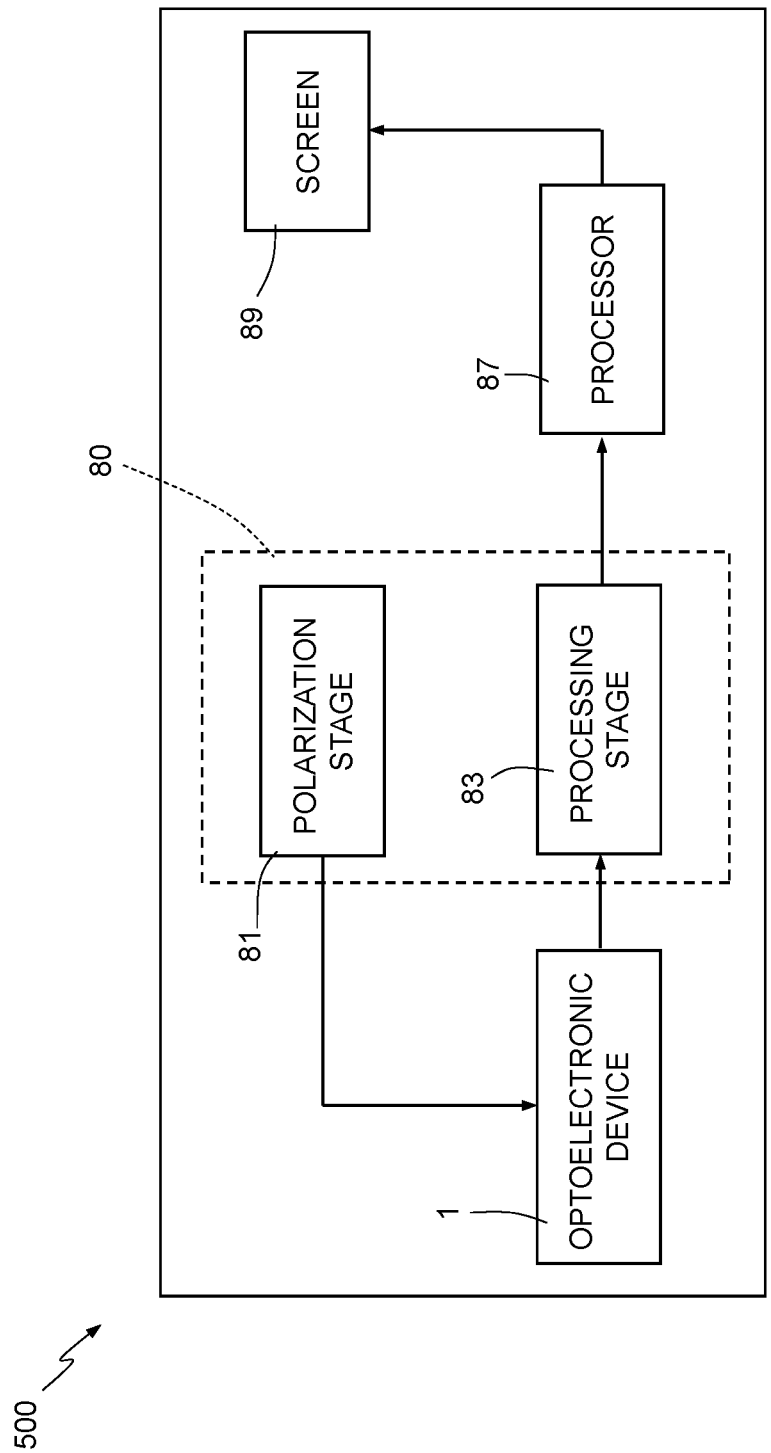
FIG. 3 is a block diagram of an electronic analysis system including the detection system shown in FIG. 1.

In consideration of the foregoing, when in use, the optoelectronic device 10 is part of an electronic analysis system 500, shown in FIG. 3. In particular, the optoelectronic device 10 is connected electrically to an external stage 80 that includes a bias stage 81. The bias stage 81 is connected electrically to the metallizations formed in the die 11 and is designed to bias the MOSFET transistor 20 and the first, second and third photodiodes 22, 24, 26, as described previously.

The external stage 80 also includes a processing stage 83 comprising for example a microcontroller unit and connected electrically to the optoelectronic device 10 such as to receive the currents (and more specifically the photocurrents) that are generated in use by the first, second and third photodiodes 22, 24, 26, hereinafter referred to as the currents IA, IB and IC respectively. These currents are generated in time-multiplexed mode to enable same to be read.

Additionally, the processing stage 83 Is connected electrically to the optoelectronic device 10, and in particular to the MOSFET transistor 20 such as to receive a signal from this latter, hereinafter referred to as the aggregated signal. This aggregated signal is indicative of an electrical magnitude of the MOSFET transistor 20, which is a function of the overall concentration of the gas mixture, regardless of the partial concentrations of the components of same (in the present example, methane, benzene, and naphthalene and anthracene).

Figure 4:
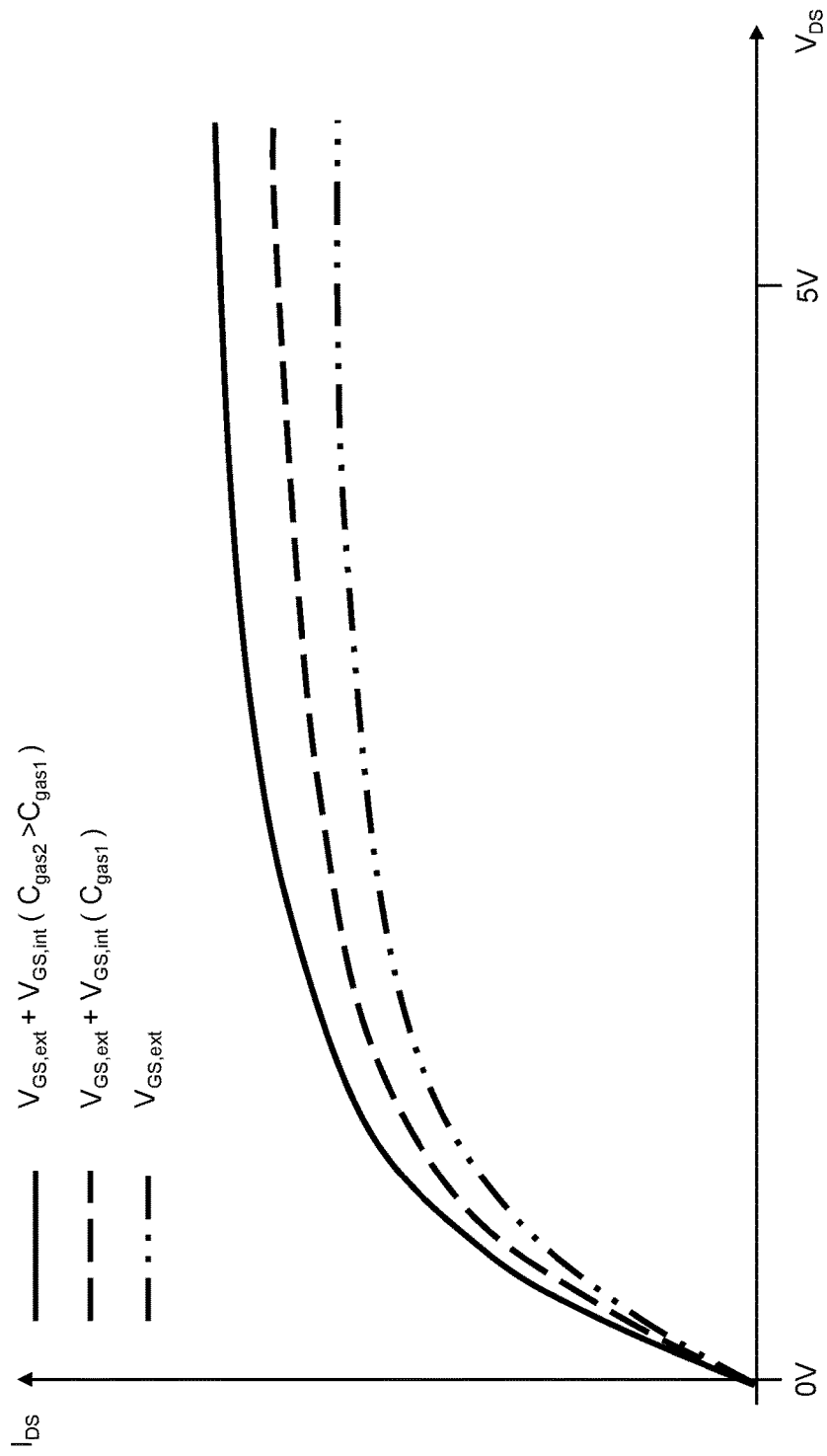
FIG. 4 shows three trends of the current IDS generated by a MOSFET transistor provided with a catalytic region, as a function of the voltage VDS.

More specifically, the presence of the catalytic region 34 ensures that, where VGSext indicates the gate-source voltage supplied by the bias stage 81, the gate-source voltage actually present on the MOSFET transistor 20 is equal to VGSext+VGSint, in which VGSint is a function of the overall concentration of the gas inside the chamber 4. To a first approximation, the equation VGSint=Ccat*σ*Cgas is true, in which Ccat indicates the concentration of catalytic material per unit of area of the catalytic region 34, while σ indicates the reaction cross section and Cgas indicates the overall concentration of gas in the chamber 4, i.e., Cgas=Cmet+Cbenz+Cnaft+Cantr, in which Cmet, Cbenz, Cnaft and Cantr indicate the concentrations of methane, benzene, naphthalene and anthracene respectively FIG. 4 shows qualitative examples of trends in the current IDS in the MOSFET transistor 20, with reference to two different values Cgas and Cgas2 for the overall concentration of gas in the chamber 4, where Cgas2>Cgas1, and with reference to a case in which there is no gas in the chamber 4. In practice, the characteristic curve IDS-VDS of the MOSFET transistor 20 is a function of the overall concentration of gas in the chamber 4. Furthermore, to a first approximation, the behavior of the MOSFET transistor 20 is not influenced by the radiation emitted by the light source 8, given that the active area of same is protected by the presence of the catalytic region 34.

Without limitation, it can therefore be assumed that the bias stage 81 supplies the voltage VGSext in a constant manner. In this case, varying the overall concentration of the gas mixture, and therefore varying the voltage VGSint, causes variations in the current IDS of the MOSFET transistor 20, which forms the aforementioned aggregated signal and represents the aforementioned electrical magnitude indicating the overall concentration of the gas mixture. It is nonetheless possible for the MOSFET transistor 20 to be current-controlled instead of voltage-controlled, in which case the processing stage 83 detects the voltage VGSint.

As previously noted, the light source 8 emits in the 200-400 nm range, i.e., in the absorption range of the polycyclic aromatic hydrocarbons (PAH). Furthermore, the light source 8 emits radiation with a spectrum at least partially overlapping the absorption range of the semiconductor material (silicon carbide) that forms the semiconductor body 12. In particular, the term useful range is hereinafter used to indicate the overlapping spectral region between the spectrum emitted by the light source 8 and the absorption range of the semiconductor material that forms the semiconductor body 12. In the present example and to a first approximation, the useful range is 200-380 nm. Furthermore, benzene, naphthalene and anthracene have non-zero absorption spectra in the aforementioned useful range, while methane has a absorption spectrum that is non-zero in the infrared range, and therefore substantially non-zero in the aforementioned useful range.

To a first approximation, the following equations are therefore true:

$IA \approx I0*\exp[-(\varepsilon benz*Cbenz+\varepsilon naft*Cnaft+\varepsilon antr*Cantr)*x]$ $IB \approx I0*\exp[-(\varepsilon naft*Cnaft+\varepsilon antr*Cantr)*x]$ $IC \approx I0*\exp[-(\varepsilon antr*Cantr)*x]$ in which I0 indicates the current value with no gas, x indicates the distance between the light source 8 and the photodiode (to a first approximation, the same for all photodiodes), while εbenz, εnaft and εantr indicate the molar absorption coefficients for benzene, naphthalene and anthracene respectively.

In practice, the first photodiode 22 is sensitive to the concentrations of benzene, naphthalene and anthracene, but not to methane. The second photodiode 24 is sensitive to the concentrations of naphthalene and anthracene only, since the equation λcutoff_1≤λτ1<λcutoff_2 is true. Conversely, the third photodiode 26 is sensitive to the concentration of anthracene only, since λcutoff_2≤λτ2<λcutoff_3.

The values of the currents IA, IB and IC therefore define a system of three equations with three unknowns, which is resolved by the processing stage 83, such as to provide three estimates of the concentrations of benzene, naphthalene and anthracene, and therefore also an overall estimate of the concentration of PAH components in the gas mixture contained in the chamber 4. The processing stage 83 therefore provides an estimate of the non-PAH components of the gas mixture (in the present example, methane) on the basis of the overall estimate of the PAH components and of the information on the overall concentration obtained via the MOSFET transistor 20. For example, the processing stage 83 may be based on the aforementioned equation VGSint=Ccat*σ*(Cmet+Cbenz+Cnaft+Cantr), to which are added the estimates for Cbenz, Cnaft and Cantr to provide an estimate of Cmet. The processing stage 83 can therefore be connected to a processor 87 of the electronic analysis system 500, which is in turn connected to a screen 89 to enable the estimates provided to be displayed.

The optoelectronic device 10 may be manufactured using the process shown in FIG. 5 and in the subsequent figures.

More specifically and as shown in FIG. 5, the semiconductor body 12, which includes the substrate 14 and the epitaxial layer 16, is pre-prepared. Furthermore, although not shown, alignment marks (not shown) are formed on the body of the semiconductor body 12, in a known manner.

Subsequently and as shown in FIG. 6, a first dielectric mask 400 is formed on the first surface S1 of the semiconductor body 12. For this purpose, a dielectric layer (not shown), formed for example by depositing TEOS oxide, for example to a thickness of 0.8 μm, is deposited on the first surface S1. Portions of the dielectric layer are then removed selectively using photolithography and related etching to expose portions of the epitaxial layer 16, in which the enriched transistor region 40 and the first, second and third enriched anode regions 224, 244, 264 are formed.

As also shown in FIG. 6, a quadruple implantation of P-type dopant (such as aluminum ions) is performed through the first dielectric mask 400 in order to form in the epitaxial layer 16 first, second, third and fourth thin layers 40', 224', 244' and 264', that appear on the first surface S1, are approximately 320 nm thick and are designed to form the enriched transistor region 40 and the first, second and third enriched anode regions 224, 244, 264 respectively. In particular, the aforementioned quadruple implantation occurs at a temperature of for example 500° C. and includes a first implantation with a dose of $5*10^{12}$ cm$^{-2}$ and energy equal to 40 keV, a second implantation with a dose of $5*10^{13}$ cm$^{-2}$ and energy equal to 100 keV, a third implantation with a dose of $1*10^{14}$ cm$^{-2}$ and energy equal to 180 keV, and a fourth implantation with a dose of $5*10^{15}$ cm$^{-2}$ and energy equal to 300 keV.

Subsequently and as shown in FIG. 7, the first dielectric mask 400 is removed by wet etching. Furthermore, a second dielectric mask 402 is formed on the first surface S1 of the semiconductor body 12. For this purpose, another dielectric layer (not shown), formed for example by depositing TEOS oxide, for example to a thickness of 0.8 μm, is deposited on the first surface S1. Portions of the other dielectric layer are then removed selectively using photolithography and related etching to expose portions of the epitaxial layer 16, in which the source region 36 and the drain region 38 of the MOSFET transistor 20 and the first, second and third cathode regions 222, 242, 262 are formed.

As also shown in FIG. 7, a multiple implantation of N-type dopant (such as phosphorus ions) is performed through the second dielectric mask 402 in order to form in the epitaxial layer 16 fifth, sixth, seventh, eighth and ninth thin layers 36', 38', 222', 242' and 262', that appear on the first surface S1, are approximately 290 nm thick and are designed to form the source region 36, the drain region 38 and the first, second and third cathode regions 222, 242, 262 respectively. In particular, the aforementioned multiple implantation occurs at a temperature of for example 500° C. and includes a first implantation with a dose of $5*10^{13}$ cm$^{-2}$ and energy equal to 30 keV, a second implantation with a dose of $1*10^{14}$ cm$^{-2}$ and energy equal to 80 keV, a third implantation with a dose of $5*10^{14}$ cm$^{-2}$ and energy equal to 120 keV, a fourth implantation with a dose of $1*10^{15}$ cm$^{-2}$ and energy equal to 150 keV, and a fifth implantation with a dose of $5*10^{15}$ cm$^{-2}$ and energy equal to 350 keV.

Subsequently and as shown in FIG. 8, the second dielectric mask 402 is removed by wet etching. A polymer layer 404 (for example formed by a resist) is then formed on the first surface S1, said layer being for example 2.5 μm thick and containing carbon atoms.

As shown in FIG. 9, the polymer layer 404 is then subjected to a pyrolysis process, by means of a thermal process at a temperature of around 800° C. for example, lasting approximately thirty minutes, in an argon environment. These operations cause the evaporation of the volatile components of the polymer layer 404 and the consequent formation of a carbon layer 406 by the carbon atoms.

As shown in FIG. 10, a thermal process is then used to activate the dopants present in the first, second, third, fourth, fifth, sixth, seventh, eighth and ninth thin layers 40', 224', 244', 264', 36', 38', 222', 242' and 262', and to reduce the reticular damage caused by the aforementioned implantations. This thermal process is carried out at a temperature of for example approximately 1650° C. and lasts for example for around thirty minutes. Furthermore, this thermal process is also carried out in an argon environment. After this thermal process has been carried out, the first, second, third, fourth, fifth, sixth, seventh, eighth and ninth thin layers 40', 224', 244', 264', 36', 38', 222', 242' and 262' form the enriched transistor region 40, the first, second and third enriched anode regions 224, 244, 264, the source region 36, the drain region 38 and the first, second and third cathode regions 222, 242, 262 respectively.

For practical purposes, the presence of the carbon layer 406 helps to prevent the formation of surface roughness on the semiconductor body 12 during performance of the aforementioned thermal dopant-activation process. Furthermore, the presence of the carbon layer 406 reduces outward diffusion of the dopants during the aforementioned thermal process.

As shown in FIG. 11, a further thermal process is then carried out in an oxygen environment at a temperature of approximately 900° C. for example, lasting for example approximately thirty minutes. This thermal process involves a reaction between the carbon in the carbon layer 406 and the oxygen, and the consequent generation of volatile components, which are dispersed. As a result, an oxidized layer 408 forms on the first surface S1.

Subsequently and as shown in FIG. 12, the oxidized layer 408 is removed, for example by wet etching. Such wet etching also involves removing a first thermal oxide layer (not shown) formed on the second surface S2 of the semiconductor body 12 during the thermal process described with reference to FIG. 11.

As shown in FIG. 13, a protective layer 410, formed for example by TEOS oxide or by a resist, is then deposited on the first surface S1 of the semiconductor body 12. Furthermore, a nickel layer 412, hereinafter referred to as the lower layer 412, is formed beneath the lower surface S2 for example by sputtering.

As shown in FIG. 14, the protective layer 410 is removed and a silicidation process is then performed, involving an annealing process lasting sixty seconds at a temperature of four example 1000° C. in a nitrogen environment. On completion of the silicidation process, there is a lower conductive region 15, that is for example 200 nm thick, beneath the second surface S2.

Subsequently and as shown in FIG. 15, a dielectric layer 420 is formed on the first surface S1. For example, the dielectric layer 420 is formed by depositing TEOS oxide and is for example 0.8 μm thick.

As shown in FIG. 16, portions of the dielectric layer 420 are then removed selectively using photolithography to expose portions of the epitaxial layer 16. The residual portions of the dielectric layer 420 form the field oxide region 28, and therefore the first, second and third windows W1, W2, W3.

A lower preliminary second-filter region 421 is then formed inside the third window W3 and over as little as possible of the portions of the field oxide region 28 laterally delimiting the third window W3. For this purpose and as shown in FIG. 17, a first layer 422 of silicon nitride is deposited onto the field oxide region 28 and onto the exposed portions of the epitaxial layer 16, and therefore inside the first, second and third windows W1, W2, W3. The first layer 422 of silicon nitride is approximately 200 nm thick.

As shown in FIG. 18, the portion of the first layer 422 of silicon nitride lying outside of the third window W3 is then removed using a photolithography process. The residual portion of the first layer 422 of silicon nitride forms the lower preliminary second-filter region 421. As also shown in FIG. 18, some of the lower preliminary second-filter region 421 can also cover portions of the field oxide region 28 laterally delimiting the third window W3.

As shown in FIG. 19, a second layer 424 of silicon nitride is deposited onto the field oxide region 28, onto the exposed portions of the epitaxial layer 16, and onto the lower preliminary second-filter region 421. The second layer 424 of silicon nitride is approximately 280 nm thick.

As shown in FIG. 20, the portions of the second layer 424 of silicon nitride other than (i) a first portion 425 of the second layer 424 of silicon nitride arranged inside the second window W2 and over as little as possible of the portions of the field oxide region 28 laterally delimiting the second window W2, and (ii) a second portion 426 of the second layer 424 of silicon nitride arranged above the lower preliminary second-filter region 421 are then selectively removed using a photolithography process. The first and second portions 425, 426 of the second layer 424 of silicon nitride are hereinafter referred to as the preliminary first-filter region 425 and the upper preliminary second-filter region 426 respectively.

As shown in FIG. 21, the insulating region 30 is then formed. In this regard, although not shown in detail, the insulating region 30 may be formed by multiple stacked layers: a first layer formed by thermal oxide (for example 10 nm thick), a second layer of silicon nitride (formed by deposition and 20 nm thick) and a third layer of silicon oxide (formed by deposition and 20 nm thick). Furthermore, the stacked layers are etched selectively following thermal treatment in a nitrogen-oxide-based environment for three hours at a temperature of 850° C., in order to reduce the defects in the insulating region 30. Details relating to the structure of the insulating region 30 and the related manufacturing steps are nonetheless irrelevant to operation of the present optoelectronic device.

Again with reference to FIG. 21, the lower preliminary second-filter region 421 and the upper preliminary second-filter region 426 are shown as a single region 427, hereinafter referred to as the preliminary second-filter region 427.

As shown in FIG. 22, a portion of the preliminary first-filter region 425 is selectively removed using a photolithography process to form a fourth window W4 and a portion of the preliminary second-filter region 427 is selectively removed using a photolithography process to form a fifth window W5. The residual portions of the preliminary first-filter region 425 and of the preliminary second-filter region 427 form the first and second filtering regions 255, 275 respectively.

As shown in FIG. 23, the source contact region 42, the drain contact region 44, the first anode contact region 226, the first cathode contact region 228, the second anode contact region 246, the second cathode contact region 248, the third anode contact region 266 and the third cathode contact region 268 are then formed. Although not shown in detail, these regions are formed by sputtering a nickel layer (not shown) and a subsequent photolithography process such as to selectively remove portions of the nickel layer by wet etching. The residual portions of the nickel layer are therefore subjected to a silicidation process which involves annealing for sixty seconds at a temperature of four example 1000° C. in a nitrogen environment.

Subsequently and as shown in FIG. 24, the source metallization 46, the gate region 32, the drain metallization 48, the first anode metallization 230, the first cathode metallization 232, the second anode metallization 240, the second cathode metallization 252, the third anode metallization 270 and the third cathode metallization 272 are formed simultaneously and in a known manner. For this purpose, one or more sputtering processes may be carried out, followed by a process for selectively removing the sputtered material.

Figure 25:
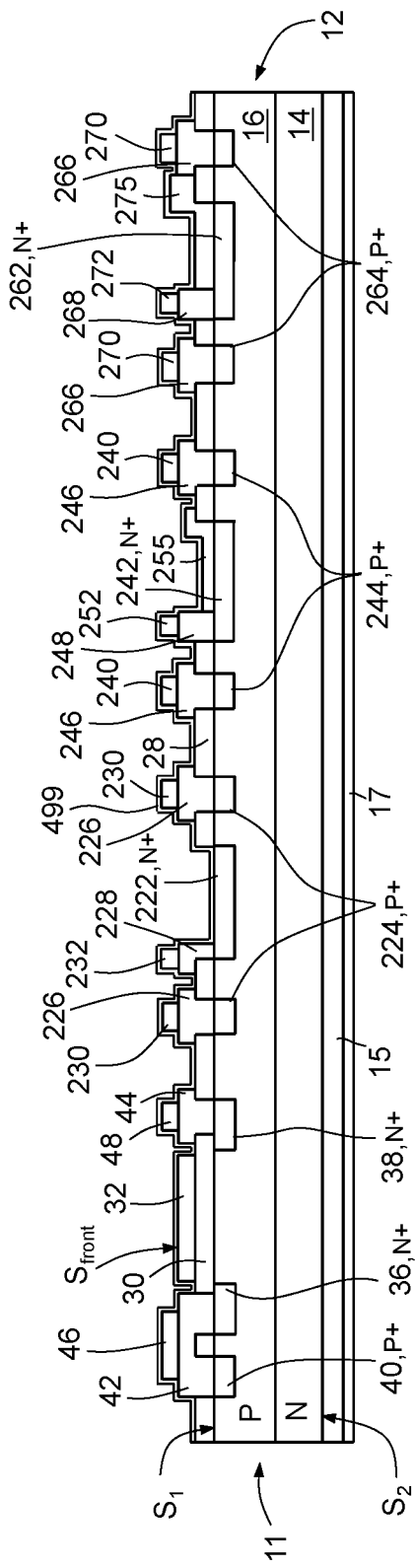

As shown in FIG. 25, a resist layer 499 is deposited on the front surface (indicated as Sfront) of the die 11. Subsequently, conductive material is sputtered beneath the lower conductive region 15 to form the lower metallization 17.

Figure 26:
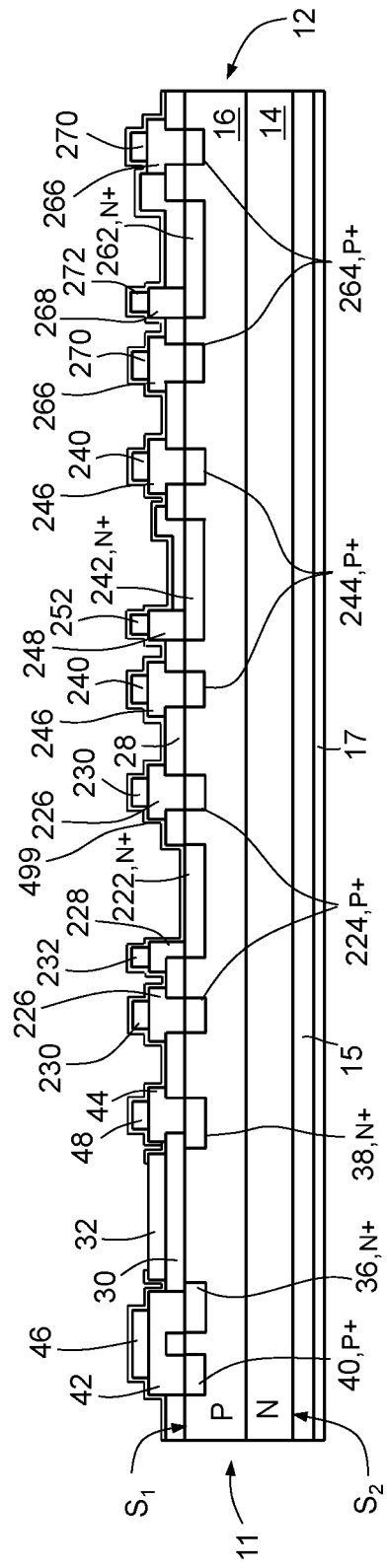

As shown in FIG. 26, a photolithography process is then carried out to selectively remove a portion of the resist layer 499 arranged above the gate region 32.

Subsequently and as shown in FIG. 27, a catalytic layer 501, for example made of palladium, platinum, tungsten or iridium and that is for example between 30 nm and 50 nm thick, is then deposited on the remaining portion of the resist layer 499 and on the gate region 32.

A lift-off process is then carried out to remove the residual portion of the resist layer 499, as well as the portion of the catalytic layer 501 on top of same. The remaining portion of the catalytic layer 501 thus forms the catalytic region 34.

The electronic device 10 can therefore be arranged inside the chamber 4, in a known manner.

The advantages achievable with the present detection system and the present optoelectronic device are clearly set out in the discussion above. In particular, the optoelectronic device is integrated and therefore small, while enabling highly sensitive detection of PAH volatile organic compounds and non-PAH volatile organic compounds at ambient temperature. Furthermore the present optoelectronic device enables high levels of sensitivity to be achieved in relation to different PAH components. Additionally, the presence of the planar MOSFET transistor makes it possible to detect the overall concentration of the gas mixture without there being a current flow in the sensitive region (the catalytic region 34), and thereby without compromising the robustness of the optoelectronic device 10.

Finally, it is obvious that the present optoelectronic device and the corresponding manufacturing process may be modified and varied without thereby moving outside the scope of the present disclosure.

For example, the number of photodiodes present in the optoelectronic device 10 may differ from the number described.

Embodiments in which the optoelectronic device has just one photodiode as well as the MOSFET transistor are also possible. In this case, the photodiode has no optical filter and, assuming that the semiconductor body is still made of silicon carbide, the optoelectronic device is able to selectively detect non-PAH volatile organic compounds and PAH compounds. In particular, the MOSFET transistor 20 can still be biased such as to generate an electrical signal indicative of the overall concentration (understood as the concentration of PAH volatile organic compounds and non-PAH volatile organic compounds), while the photodiode generates a current indicative of the concentration of the PAH compounds only, such as to determine the concentration of non-PAH volatile organic compounds from the difference.

In general, it is also possible for the semiconductor body 12 to be made of a semiconductor material other than silicon carbide, such as silicon, which is able to absorb radiation at wavelengths less than 1100 nm. In embodiments still based on absorption in the ultraviolet range, the semiconductor body may be made of gallium nitride, for example.

Similarly, the materials used to make the optoelectronic device may differ from those described. For example, the optical filters may be made of metal oxides or oxynitrides rather than silicon nitride.

It is also possible for the semiconductor body to have one or more epitaxial layers that are different from those described.

The optical filters may be formed by interference filters instead of adsorption filters, in which case same maybe formed by corresponding Bragg gratings. In this case, the optical filters may have a passband response with an upper limit given by the upper limit of the absorption range of the semiconductor material.

Finally, the type of conductivity may be the inverse of that described.

The various embodiments described above can be combined to provide further embodiments. These and other changes can be made to the embodiments in light of the above-detailed description. In general, in the following claims, the terms used should not be construed to limit the claims to the specific embodiments disclosed in the specification and the claims, but should be construed to include all possible embodiments along with the full scope of equivalents to which such claims are entitled. Accordingly, the claims are not limited by the disclosure.

The invention claimed is:

1. An optoelectronic device for detecting volatile organic compounds, comprising:
a die including a semiconductor body made of a semiconductor material with an absorption spectrum range, said optoelectronic device being optically couplable to an optical source designed to emit radiation with a spectrum at least partially overlapping said absorption spectrum range;
a MOSFET transistor formed in the semiconductor body, wherein the MOSFET transistor is planar and includes a gate region and a catalytic region that is arranged on the gate region such that, in the presence of a gas mixture including volatile organic compounds, the MOSFET transistor is configured to be biased to generate an electrical signal indicating an overall concentration of the gas mixture within a volume; and
a first photodiode configured to generate, when said optoelectronic device is optically coupled to set optical source, a first photocurrent that is a function of a concentration of one or more polycyclic aromatic hydrocarbons present in said gas mixture.

2. The optoelectronic device according to claim 1, in which said semiconductor body includes a front region that has a first type of conductivity and defines a front surface that delimits the semiconductor body, and in which said first photodiode includes a first cathode region that has a second type of conductivity and extends inside the front region from the front surface.

3. The optoelectronic device according to claim 2, further comprising a second photodiode integrated into said die, said second photodiode including:
a second cathode region that has the second type of conductivity and extends inside the front region from the front surface,
a first optical filter arranged above the second cathode region and is configured to filter ultraviolet radiation at wavelengths greater than a first threshold value.

4. The optoelectronic device according to claim 3, further comprising a third photodiode integrated into said die, said third photodiode including:
a third cathode region that has the second type of conductivity and extends inside the front region from the front surface,
a second optical filter arranged above the third cathode region and is configured to filter ultraviolet radiation at wavelengths greater than a second threshold value that is greater than the first threshold value.

5. The optoelectronic device according to claim 4, in which said second and third photodiodes are configured to generate second and third photocurrents respectively, and in which said first and second optical filters are configured such that, when the gas mixture contains benzene, naphthalene and anthracene, the first photocurrent is a function of concentrations of benzene, naphthalene and anthracene, the second photocurrent is a function of the concentrations of naphthalene and anthracene, and the third photocurrent is a function of the concentration of anthracene.

6. The optoelectronic device according to claim 5, in which said first and second optical filters are made of a material selected from silicon nitride, a metal oxide, and an oxynitride.

7. The optoelectronic device according to claim 1, in which said absorption spectrum range of the semiconductor material is not zero in the ultraviolet range.

8. The optoelectronic device according to claim 7, in which said semiconductor body is made of silicon carbide.

9. A detection system, comprising:
an optical source configured to emit radiation with a spectrum; and
an optoelectronic device optically coupled to the optical source and including:
a die including a semiconductor body made of a semiconductor material with an absorption spectrum range at least partially overlapping the spectrum of the radiation;
a MOSFET transistor formed in the semiconductor body, wherein the MOSFET transistor is planar and includes a gate region and a catalytic region that is arranged on the gate region such that, in the presence of a gas mixture including volatile organic compounds, the MOSFET transistor is configured be biased to generate an electrical signal indicating an overall concentration of the gas mixture within a volume; and
a first photodiode configured to generate, when said optoelectronic device is optically coupled to set optical source, a first photocurrent that is a function of a concentration of one or more polycyclic aromatic hydrocarbons present in said gas mixture.

10. The detection system according to claim 9, in which said optical source is configured to emit ultraviolet radiation.

11. The detection system according to claim 9, including a chamber containing the optoelectronic device and the optical source, said chamber being fluidly accessible to said gas mixture.

12. An analysis system comprising:
a detection system including:
an optical source configured to emit radiation with a spectrum; and
an optoelectronic device optically coupled to the optical source and including:
a die including a semiconductor body made of a semiconductor material with an absorption spectrum range at least partially overlapping the spectrum of the radiation;
a MOSFET transistor formed in the semiconductor body, wherein the MOSFET transistor is planar and includes a gate region and a catalytic region that is arranged on the gate region such that, in the presence of a gas mixture including volatile organic compounds, the MOSFET transistor is configured be biased to generate an electrical signal indicating an overall concentration of the gas mixture within a volume; and
a first photodiode configured to generate, when said optoelectronic device is optically coupled to set optical source, a first photocurrent that is a function of a concentration of one or more polycyclic aromatic hydrocarbons present in said gas mixture,
a bias stage configured to bias said MOSFET transistor and said first photodiode, and
a processing stage configured to receive and process said electrical signal and said first photocurrent.

13. The analysis system according to claim 12, wherein the detection system includes a chamber containing the optoelectronic device and the optical source, said chamber being fluidly accessible to said gas mixture.

14. A process for manufacturing an optoelectronic device for detecting volatile organic compounds, the process comprising:
forming, on a die including a semiconductor body, a planar MOSFET transistor, said forming the MOSFET transistor including forming a gate region on the semiconductor body and forming a catalytic region that is arranged on the gate region;
forming a first photodiode, wherein forming the first photodiode includes forming a first cathode region that extends inside the semiconductor body;
forming a second photodiode on said die, wherein forming the second photodiode includes:
forming a second cathode region that extends inside the semiconductor body, and
forming a first optical filter arranged above the second cathode region and configured to filter ultraviolet radiation at wavelengths greater than a first threshold value;
forming a third photodiode on said die, wherein forming the third photodiode includes:
forming a third cathode region that extends inside the semiconductor body, and
forming a second optical filter arranged above the third cathode region and configured to filter ultraviolet radiation at wavelengths greater than a second threshold value that is greater than the first threshold value, wherein forming the first and second optical filters includes:
forming a preliminary region of a selected material on the third cathode region;
subsequently forming a layer of said selected material above the preliminary region and the second cathode region; and
subsequently selectively removing portions of said layer of said selected material such that a first residual portion of said layer of said selected material forms the first optical filter, and that a second residual portion of said layer of said selected material forms the second optical filter along with said preliminary region.

15. The process according to claim 14, in which said semiconductor body includes a front region that has a first type of conductivity and defines a front surface that delimits the semiconductor body, wherein forming the first photodiode includes forming the first cathode region with a second type of conductivity and extending inside the front region from the front surface.

16. The process according to claim 15, further comprising:
forming a dielectric region of said MOSFET transistor above said front surface, prior to forming the gate region and the catalytic region.

17. The process according to claim 14, further comprising:
forming a resist layer above the gate region, the first cathode region and the first and second optical filters,
selectively removing a portion of the resist layer arranged above the gate region, and subsequently
forming a layer of catalytic material above the residual portion of the resist layer and the gate region, and subsequently
using a lift-off process to remove a portion of the layer of catalytic material arranged on the residual portion of the resist layer.

* * * * *